United States Patent [19]

Kriesel

[11] Patent Number: 5,019,047
[45] Date of Patent: May 28, 1991

[54] FLUID DELIVERY APPARATUS

[75] Inventor: Marshall S. Kriesel, St. Paul, Minn.

[73] Assignee: Science Incorporated, Bloomington, Minn.

[21] Appl. No.: 367,304

[22] Filed: Jun. 16, 1989

[51] Int. Cl.$^5$ ............................................. A61M 37/00
[52] U.S. Cl. .................................... 604/132; 604/131; 604/246; 604/890.1; 128/DIG. 12
[58] Field of Search ................................. 604/131–132, 604/149, 246, 257, 153, 212, 216–217, 890.1, 122, 126; 128/DIG. 12

[56] References Cited

U.S. PATENT DOCUMENTS

| | | |
|---|---|---|
| 3,151,616 | 10/1964 | Selfon . |
| 3,153,414 | 10/1964 | Beall et al. . |
| 3,468,308 | 9/1969 | Bierman . |
| 3,469,578 | 9/1969 | Bierman .................. 604/132 |
| 3,565,292 | 3/1970 | Jinotti . |
| 3,677,444 | 8/1972 | Merrill ..................... 604/132 X |
| 3,780,732 | 12/1973 | Leibinsoh . |
| 3,895,741 | 7/1975 | Nugent . |
| 3,993,069 | 11/1976 | Buckles et al. . |
| 4,201,207 | 5/1980 | Buckles et al. . |
| 4,386,929 | 6/1983 | Perry et al. . |
| 4,419,096 | 12/1983 | Leeper et al. . |
| 4,430,078 | 2/1984 | Sprague . |
| 4,432,468 | 2/1984 | Siff et al. . |
| 4,507,116 | 3/1985 | Leibinsohn . |
| 4,511,355 | 4/1985 | Franetzki et al. .................. 604/131 |
| 4,539,004 | 9/1985 | Eckenhoff et al. .................. 604/131 |
| 4,551,136 | 11/1985 | Mandl . |
| 4,645,486 | 2/1987 | Beal et al. ............................. 604/4 |
| 4,769,008 | 9/1988 | Hessel . |
| 4,838,887 | 6/1989 | Idriss ............................... 604/891.1 |

FOREIGN PATENT DOCUMENTS

2043594 10/1980 United Kingdom ............... 604/246

Primary Examiner—C. Fred Rosenbaum
Assistant Examiner—Corrine Maglione
Attorney, Agent, or Firm—James E. Brunton

[57] ABSTRACT

An apparatus for accurately infusing medicinal agents into an ambulatory patient at specific rates over extended periods of time. The apparatus is of a compact, low profile, laminate construction and includes an elastic distendable membrane, which, in cooperation with a thin planar base, defines a fluid chamber having a fluid outlet. Disposed within the fluid chamber is a thin fluid permeable member which precisely controls the rate of fluid flow through the fluid outlet.

32 Claims, 7 Drawing Sheets

FLUID DELIVERY APPARATUS

BACKGROUND OF THE INVENTION

FIELD OF THE INVENTION

The present invention relates generally to fluid delivery devices. More particularly, the invention concerns an improved apparatus for infusing medicinal agents into an ambulatory patient at specific rates over extended periods of time.

DISCUSSION OF THE INVENTION

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldly and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films and similar materials, which, in cooperation with a, plate-like base defines a fluid chamber that contains the fluid which is to be dispensed. The elastomeric film membrane controllably forces fluid within the chamber into fluid flow channels provided in the base. In one form of the apparatus of the invention, a thin, planar shaped flow rate control member is strategically located within the chamber to precisely control the rate of flow of the liquid toward the fluid flow channels. The flow rate control member can be very thin and can be selected to have a very precise degree of permeability so that the rate of flow of fluid into the fluid flow channels can be controlled with great accuracy.

The use of state of the art thin membranes and films permits the construction of compact, low profile, laminated structures which are easy to use and inexpensive to manufacture. When the devices of the invention are to be used with ambulatory patients they are constructed of flexible materials and are provided with a thin adhesive backing which permits the device to be conveniently self-affixed to the patient's arm or other parts of the body.

The apparatus of the invention can be used with minimal professional assistance in an alternate health care environment, such as the home. By way of example, devices of the invention can be used for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

SUMMARY OF THE INVENTION

It is an object of the present invention to provide an apparatus for expelling fluids at a precisely controlled rate which is of a compact, low profile, laminate construction. More particularly, it is an object of the invention to provide such an apparatus which can be used for the precise infusion of pharmaceutical fluids to an ambulatory patient at controlled rates over extended periods of time.

It is another object of the invention to provide an apparatus of the aforementioned character which is highly reliable and easy-to-use by lay persons in a non-hospital environment.

Another object of the invention is to provide an apparatus which can be factory prefilled with a wide variety of medicinal fluids or one which can readily be filled in the field shortly prior to use.

Another object of the invention is to provide an infusion device in which fluids can be delivered either at a fixed rate or at variable rates and one which is operational in all altitudes and attitudes.

Still another object of the invention is to provide an apparatus of the class described which is soft, conformable and compliant so as to readily conform to the patient's anatomy proximate the point of infusion.

Yet another object of the invention is to provide an apparatus as described in the preceding paragraph which is provided with a thin, flexible foam backing with adhesive for self-attachment. The apparatus can be unobtrusively worn under clothing.

A further object of the invention is to provide a low profile, fluid delivery device of laminate construction which can be manufactured inexpensively in large volume by automated machinery.

Another object of the invention is to provide a device of the character described in which fluid is dispelled from the apparatus through either an integral infusion needle, or through a luer type connector, by a thin, distendable membrane cooperatively associated with a thin, plate-like base.

Another object of the invention is to provide an apparatus of the aforementioned character in which the distendable member is permeable to gases at least in one direction, whereby gases within the medicinal agent can be released from the fluid chamber and not injected into the patient.

Still another object of the invention is to provide an apparatus as described in the preceding paragraphs in which the rate of fluid flow from the apparatus is precisely controlled by a thin planar shaped, fluid permeable member which forms a part of the low profile, laminate construction of the apparatus.

DESCRIPTION OF THE INVENTION

Figures 1, 2, 6, 7, 9:
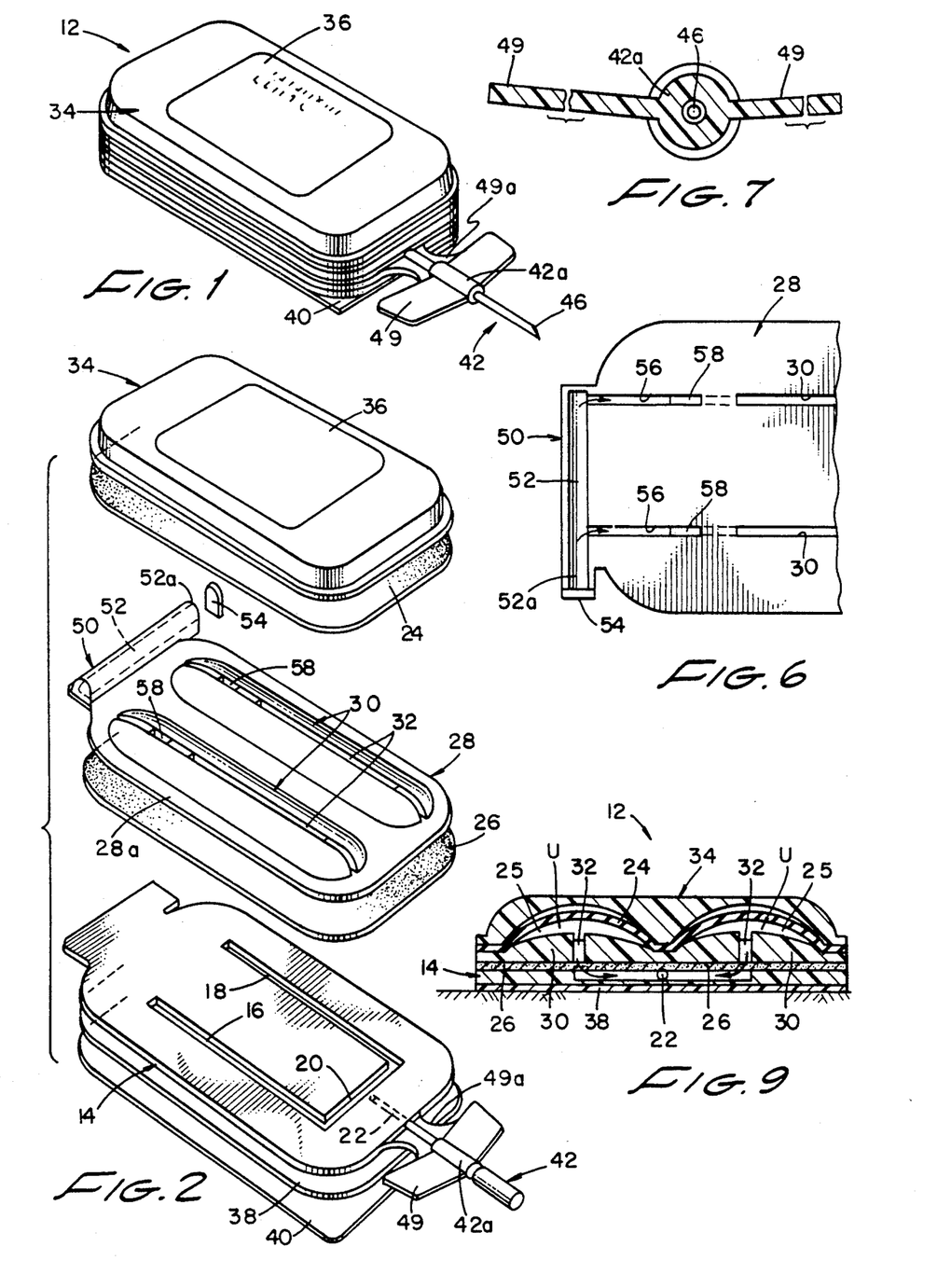
FIG. 1 is a generally perspective view of one form of the fluid dispensing apparatus of the invention.
FIG. 2 is an exploded, generally perspective view of the apparatus of FIG. 1.
FIG. 6 is a fragmentary view taken along lines 6—6 of FIG. 4.
FIG. 7 is a cross sectional view taken along lines 7—7 of FIG. 4.
FIG. 9 is a cross sectional view taken along lines 9—9 of FIG. 8.
Figures 3, 5:
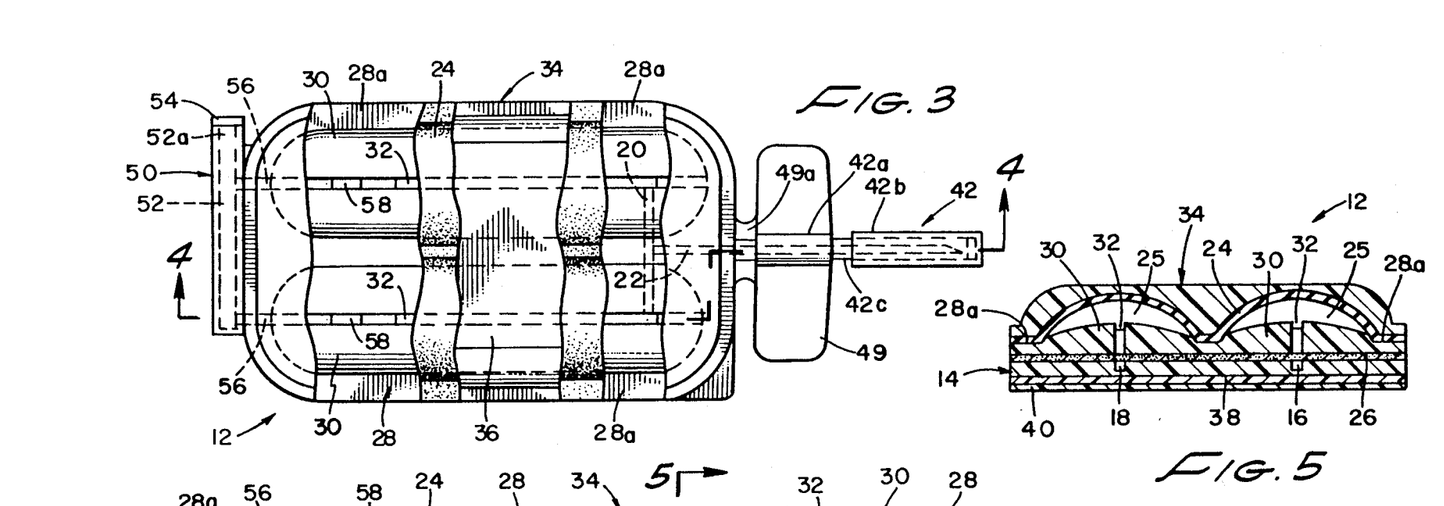
FIG. 3 is a top view of the apparatus partly broken away to show internal construction.
FIG. 5 is a cross sectional view taken along lines 5—5 of FIG. 4.
Figures 4, 8:
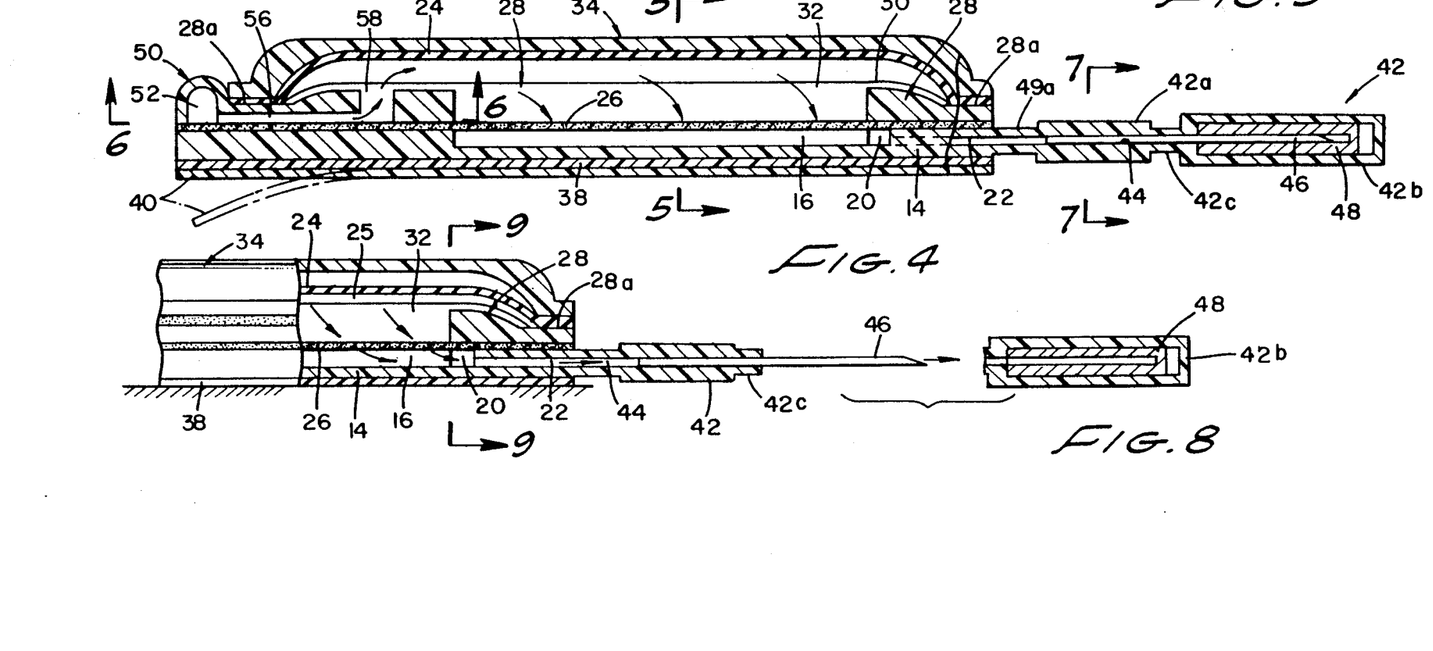
FIG. 4 is an enlarged cross sectional view taken along lines 4—4 of FIG. 3.
FIG. 8 is a view similar to FIG. 4, but illustrating the separation of the molded needle cover from the device.

Referring to the drawings and particularly to FIGS. 1 through 9, one embodiment of the apparatus for use in infusing medicinal fluids into a patient is there illustrated and generally designated by the numeral 12. As indicated in FIG. 1, the apparatus of this form of the invention comprises a laminate, or layered, structure made up of a plurality of thin plate-like components. As best seen by referring to FIG. 2, the apparatus comprises a thin, generally planar plate-like base 14, having a pair of flow rate control channels provided here as longitudinally extending fluid conduits 16 and 18. Conduits 16 and 18 are interconnected by a fluid transfer manifold, or transverse conduit 20, which, in turn, is interconnected with a fluid outlet passageway 22. A thin, generally planar distendable elastomeric membrane, or member, 24 cooperates with base 14 to form a chamber 25 (FIG. 4). Member 24 is distendable out of plane in the manner shown in FIG. 4 by the introduction of fluid into the chamber under pressure. As the distendable member 24 is distended by the fluid pressure, internal stresses are formed in the member which continuously urge it to return to its original planar configuration. The method of introduction of fluids into chamber 25 will presently be described.

Forming an important aspect of the apparatus of the invention is the provision of flow control means which is disposed internally of chamber 25 for controlling the rate of fluid flow through the outlet 22 formed in base member 14. In the embodiment of the invention here shown, the flow control means is provided in the form of a thin, permeable member 26 which is superimposed over base 14 in the manner shown in FIG. 4. As will presently be described, member 26 precisely controls the rate of fluid flow from chamber 25 into fluid conduits 16, 18 and 20 formed in base 14. It is this precise control of the rate of fluid flow which enables infusion into the patient of medicinal fluids at an extremely precise rate over extended periods of time ranging from several hours to in excess of 24 hours depending on sized reservoir volume.

Superimposed over flow control member 26 is a distendable membrane engagement means. This means is here provided in the form of a generally planar member 28 having a peripheral portion 28a to which the margins of distendable member 24 are bonded, as by adhesive or thermo-bonding. Member 28 also has a pair of longitudinally extending, spaced apart upstanding protruberances 30. Each of the protruberances 30 is provided with a longitudinally extending first fluid passageway or conduit 32. When the apparatus is assembled in the manner shown in FIG. 9, passageways 32 are superimposed over fluid conduits 16 and 18 and protruberances 30 extend upwardly into fluid chamber 26 so as to define ullage "U" within chamber 25. In operation of the device, as distendable membrane 24 attempts to return to its original planar configuration (FIG. 9), it will move toward engagement with the upper surfaces of protruberances 30 and in so doing will efficiently force the fluid contained within chamber 25 uniformly through the flow control member 26 and into passageways 16 and 18. The configuration of protruberances 30 ensure that all of the fluid within chamber 25 will be dispelled therefrom as the membrane returns toward its starting configuration. Passageways 16, 18, and 32 can be alternately configured to provide various degrees of fluid exposure to rate control membrane 26 whereby the active surface area of membrane 26 is increased or decreased.

Superimposed over the assembly comprising base 14, distendable membrane 24, flow control member 26, and distendable membrane engaging member 28 is a porous plastic cover 34 which functions to provide a superstructure and a venting means for venting gases, if any, contained within the medicinal agent. Affixed to the top of cover 34 is a medicant and use instruction label 36 which can be used to identify the medicinal fluid contained within chamber 25 of the device.

Affixed to the bottom of base 14 is a cushioning means shown here as a thin, planar shaped foam pad 38. Foam pad 38 is provided with adhesive on both its upper and lower surfaces. The adhesive on the upper surface of pad 38 enables the pad to be affixed to the lower surface of base 14. As indicated in FIGS. 2 and 4, a peel strip 40 is connected to the bottom surface of foam pad 38 by the adhesive provided thereon. When the device is to be used, peel strip 40 can be stripped away from pad 38 so that the adhesive on the lower surface of the foam pad 38 can be used to releasably affix the apparatus of the invention to the anatomy of the patient.

Turning now to FIGS. 4 and 8, a needle assembly 42 is integrally formed with base 14. Needle assembly 42 which includes a distal portion 42a and a proximal portion 42b, is provided with a longitudinally extending bore 44. As best seen in FIG. 4, bore 44 is in communication with outlet passageway 22 formed in base 14. Fixedly received within that portion of passageway 44, which extends through distal portion 42a, is a hollow infusion needle 46 of the character typically used for injecting fluids into a patient. The fluid outlet end of needle 46 is received within that portion of passageway 44 which extends through proximal portion 42b. Intermediate portions 42a and 42b is a reduced diameter frangible portion 42c which can be broken so as to separate portions 42a and 42b to expose the outlet end of needle 46 in the manner shown in FIG. 8. Also forming a part of proximal portion 42b is a protective sheath 48 for encapsulating and protecting needle 46. Needle assembly 42 also includes web means for further assisting in securing and maintaining the needle in an appropriate invasive position to preclude inter-vascular trauma. The web means are here provided as a soft, flexible butterfly assemblage 49, which, as shown in FIGS. 1 and 7, is integrally formed with base 14 and joined therewith by webbing 49a. Butterfly assembly 49 also provides appropriate surface area for tape adhesion covering the injection site.

Turning now to FIGS. 2, 3, 4 and 6, the distendable membrane engagement element 28 which comprises the means for creating an ullage within chamber 25, also includes an upstanding transversely extending portion 50 having a fluid passageway 52 extending therethrough. In the present embodiment of the invention, the open end 52a of passageway 52 is closed by a closure member 54 which is adapted to sealably close passageway 52 after chamber 25 has been filled with the selected medicinal agent. Passageway 52 can also be closed by any suitable means such as thermal or mechanical sealing. As best seen by referring to FIG. 4, passageway 52 is in communication with a pair of longitudinally extending passageways 56 formed in element 28. Passageways 56 are, in turn, in communication with chamber 25 via passageways 58. As illustrated in FIG. 2, passageways 58 extend through protuberances 30 and are disposed in the ends of protuberances 30 located proximate transversely extending passageway 52.

The apparatus of this first embodiment of the invention is adapted to be filled with the selected medicinal fluid at time of manufacture. This is accomplished by removal of plug 54 so that fluid under pressure can be forced into passageway 52 and thence into chamber 25 via passageways 56 and 58. As the fluid under pressure flows through passageways 58, it will cause the membrane 24 to distend upwardly into initial engagement with cover 34 in the manner shown in FIG. 4. After chamber 25 has been filled with the medicinal fluid, closure plug 54 is bonded or otherwise affixed in place within the open end 52a of conduit 52 so as to seal chamber 25 with respect to atmosphere.

So long as needle assembly 42 remains intact in the manner shown in FIG. 4, the fluid will be retained within chamber 25. However, upon twisting and breaking the frangible section 42c so that portion 42b of the needle assembly can be removed as shown in FIG. 8, distendable membrane 24 will begin to expel fluid through the needle 46. The rate of expulsion of fluid is, of course, controlled by the permeable membrane 26 which is disposed intermediate the fluid flow passageways 32 of member 28 and fluid flow passageways 16 and 18 formed in base 14.

As previously mentioned, the state of the art materials used in the construction of the apparatus of the invention markedly contribute to the reliability, accuracy and manufacturability of the apparatus. Before discussing the alternate forms of the invention shown in the drawings, a brief review of the materials used in constructing the apparatus is in order.

With respect to the base 14, a wide variety of materials can be used, including; metals, rubber or plastics that are compatible with the liquids they contact and are preferably not non-allergenic. Examples of such materials are stainless steel, aluminum, latex rubber, butyl rubber, nitrile rubber, polyisiprene, styrene-butadiene copolymer, silicones, polyolefins such as polypropylene and polyethylene, polyesters, polyurethane, polyamides and polycarbonates. Manufacturers of suitable materials include; Dow Corning of Midland, Mich., General Electric of Schenectady, N.Y. and Shell Chemical Company of Houston, Tex., DuPont Chemical of Wilmington, Del., and Eastman Chemical of Kingsport, Tenn.

Considering next the important flow control means, or member 26, precision microflow through this important component is a convective flow delivery process with controllable delivery rates between 0.1 to 4.5 milliliters per hour. Depending on the medicinal agent to be delivered and the required flow rate regime, several microporous membranes can be employed, including asymmetric substrate based films such as cellulose acetate, cellulose acetate buterate, and ethyl cellulose. These membrane films may vary from 20 microns to 100 microns thick and can be made of a porous substrate with a controlled skin where the active porosity can vary from angstroms to 50 microns in diameter. Additionally, other acrylic resins can also be used for thin film, delivery membranes such as poly-methylmethacrylate (PMM) and polysulfone on PVC also with approximately 2 microns thickness of skin of active membrane surface on up to 100 microns of substrate backing.

Other matrix polymer systems are also candidates for microfilm membranes and include PCCE copolyesters and nylon PEBAX-polyethersteramide (PEEA), as well as PTFE, PVDF, P-P mixed ester cellulose and certain other polycarbonates. Manufacturers of these materials include; Bend Research (Cellulose Acetates, polysulfones), Eastman Chemical (PCCE Copolyester #9966), Atochem (PEBAX Nylon), Dupont (Hytrel), Rohm Pharmaceuticals (Acrylic Resins) and Millipore (PTFE), PVDF and mixed ester cellulose).

Considering next the elastic distendable membrane 24, this important component can be manufactured from several alternate materials including rubbers, plastics and other thermoplastic elastomers. These include latex rubber, polyisoprene (natural rubber), butyl rubber, nitrile rubber, other homopolymer, copolymers (random, alternating, block, graft, crosslink and starblock), mechanical poly-blends and interpenetrating polymer networks.

Examples of materials found particularly well suited for this application include; silicone polymers (polysiloxanes) (high performance silicone elastomers made from high molecular weight polymers with appropriate fillers added. These materials are castable into thin film membrances and have high permeability (which allows maximum transport of vapor and gas), high bond and tear strength and excellent low temperature flexibility and radiation resistance. Additionally, silicone elastomers retain their properties over a wide range of temperature ($-80°$ to $200°$ C.) are stable at high temperatures, and exhibit tensile strengths up to 2,000 lb./in$^2$ elongation up to 600%.

Further, silicone (polyorganosiloxanes) are thermally stable, hydrophobic organometallic polymers with the lowest P-P interaction (of all commercially available polymers. This fact coupled with the flexibility of the backbone results in a low Tg ($-80°$ C.) and an amorphous rubbery structure for the high MW (polydimethylsiloxanes). Silicone rubber membranes are considerably more permeable to gases than membranes of any other polymer. Depending on the medicinal fluid used and the filling of the storage mode, which will determine the desired mass transport characteristics of the membrane (permeability and selectivity), other materials of choice include polyurethane-polysiloxane copolymers, blends and IPN's. By example, polydimethylsiloxane (PDMS) and polyurethane (PU) multicomponent IPN containing 10%-20% weight of PU shows enhanced initial modulus relative to that of PDMS itself.

Interpenetrating polymer networks (IPNS) are unique blends of cross-linked polymers containing essentially no covalent bonds, or grafts between them. True IPNS are also homogeneous mixtures of component polymers. Further examples of an additional candidate materials would be a polyurethane-polysiloxane (IPN) bilaminated with a polyparaxylene or alternately bilamination of polydimethylsiloxane (PDMS) and polyparaxylene. Coextruded laminates of this type can be selected according to the desired gas permeability for vapor and $O_2$, $N_2$ and $CO_2$ diffusion and their specific selectivity requirements as well as for direction of gas migration when appropriately layered.

Manufacturers of materials suitable for use in the construction of the distendable membrane, include Dow Chemical, General Electric, B.P. Polymers, Mobay Chemical, Shell Oil Corp., Petrarch Systems, DuPont,Concept Polymers and Union Carbide Corp.

With respect to the structural cover 34, in certain embodiments of the invention, this component can be produced from one of several polymer groups. The plastic structure of this component typically contains an intricate network of open celled omni directional pores. The pores can be made in average sizes for 0.8 micron to 2,000 micron and, gives the porous plastic a unique combination of venting filtering, wicking and diffusing capability and structural strength. Further, the material is strong, lightweight, has a high degree of chemical resistance and depending on the particular configuration of the apparatus, can be flexible. The degree of hardness can range from soft, resilient or rigid, and depending on the specific micro diameter range desired, the following polymers can be employed: Polypropylene(PP), Ultra high molecular weight polyethylene (UHMW PE), High density polyethylene (HDPE), Polyvinylidene Fluoride (PVDF), Ethylene-vinyl acetate (EVA), Styrene Acrylonitrile (SAN), Polytetrafluoroethylene (PTFF). A suitable source of these materials is Porex Technologies of Fairburn, Georgia.

An alternate material for use in constructing the covers, as for example, covers 34 and 80, when the cover is to serve as a non-permeable gas barrier, is a material sold by B-P Chemicals International of Cleveland, Ohio, under the name and style "Barex". This material, which can also be used to alternately construct base 14 and element 28, is a clear rubber modified Acrylonitrile Copolymer which has wide application in the packaging industry because of its superior gas barrier, chemical resistance and extrusion (thermoforming) and injection molding capabilities. Structures using this material can be manufactured in either monolayer or coextrusion (with such other materials as polyethylene, polypropylene, polystyrene and other modified styrenes). Combinations of different materials can be used to enhance the desired physical properties of the thermoformed part.

Finally, the foam pad adhesive 38 and peel strip 40 is preferably composed of a thin (1/32") 30 mil closed cell polyethylene (PE) foam double coated with a non-sensitizing acrylic pressure sensitive adhesive (PSA), and 90 lb. white polyethylene coated release liner (peel strip). This foam is also available in 1/16 inch and ⅛ inch thickness. The foam is stretchable, soft, elastic, conformable, cushioning, hypoallergenic, and is desirable for application where sustained use is required. The material is available from the 3M Company of Saint Paul, Minn. and from Betham Corporation of Middlesex, N.J.

Turning now to FIGS. 10 through 17, another embodiment of the invention is thereshown. The apparatus of this form of the invention is similar in many respects to that previously described and like numbers are used to identify like components. Unlike the apparatus illustrated in FIGS. 1 through 9 which has a thermo sealed filling port, the apparatus of this second form of the invention is adapted to be filled using a hypodermic syringe. The device may have a cover made of the same material as cover 34, or may have a different type of impermeable cover, the function of which will presently be described.

Figures 10, 17:
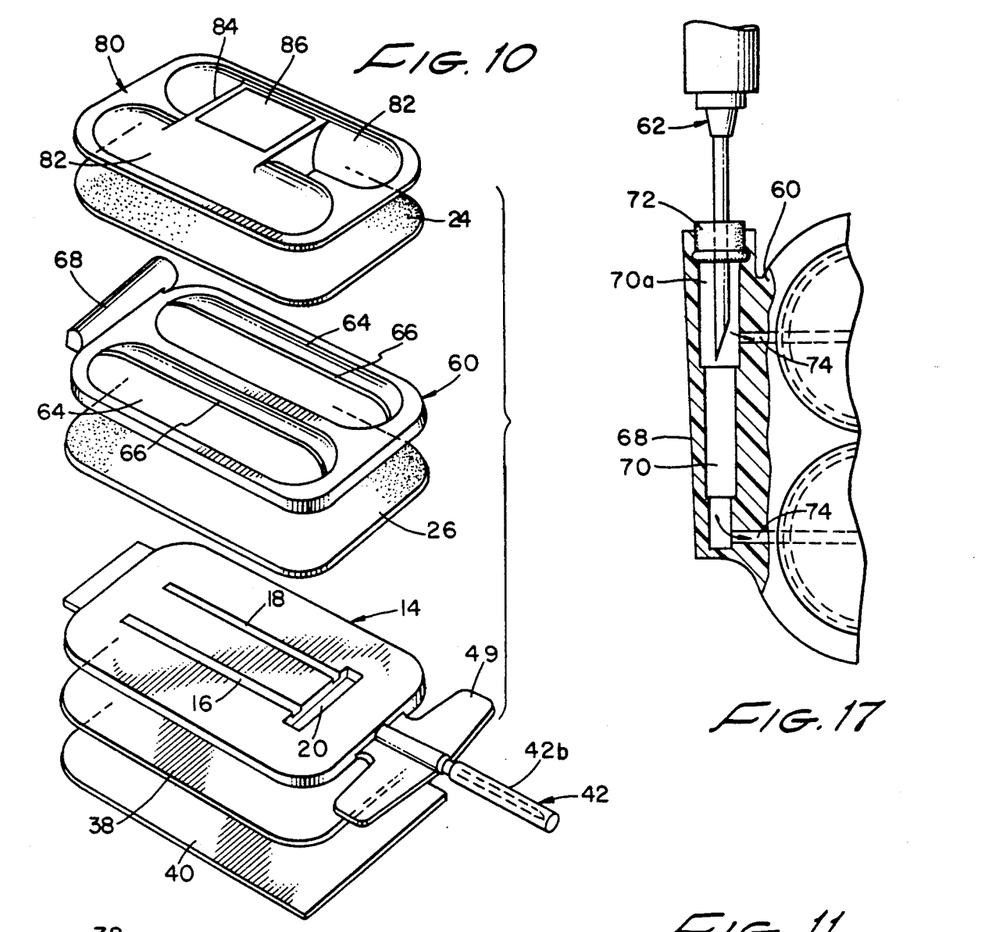
FIG. 10 is a generally perspective exploded view of another embodiment of the fluid dispensing apparatus of the present invention.
FIG. 17 is a greatly enlarged fragmentary view illustrating the method of fluid fill of the apparatus of this form of the invention.
Figure 11:
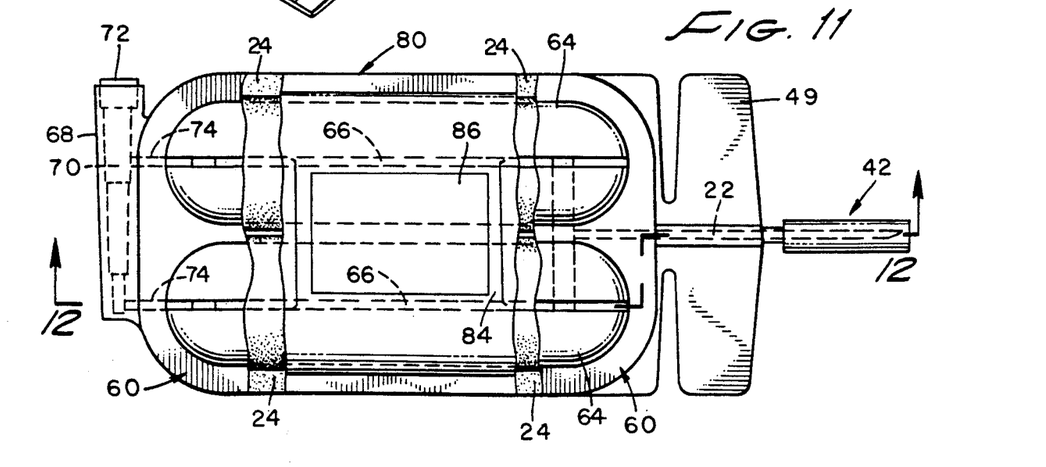
FIG. 11 is a top view of the apparatus shown in FIG. 10.

Referring to FIG. 10, the apparatus can be seen to comprise a base 14, a distendable member 24 and a flow control member 26 all of which are of the same general character and function in the same manner as in the earlier described embodiment of the invention. The distendable member engaging element 60 is of slightly different construction and includes filling means which enables chamber 25 to be filled using a hypodermic syringe and needle of the character identified in FIG. 17 by the numeral 62. Element 60 is superimposed over flow control member 26 and includes a pair of longitudinally extending, spaced apart upstanding protuberances 64. Each protuberance 64 is provided with fluid passageways 66 which communicate with fluid passageways 16 and 18 provided in base 14. Element 60 also includes an upstanding transversely extending portion 68 having a fluid passageway 70 extending therethrough (FIGS. 10, 11 and 17). In this second embodiment of the invention, the open end 70a of passageway 70 is closed by a septum means for receiving a hypodermic needle. The septum means is here provided as a septum 72 which is adapted to sealably close the open end 70a of passageway 70. Septum 72 is constructed of a self-sealing, puncturable material such as silicone-SEBS (a composite incorporating a silicone interpenetrating network (IPN) into a styrene-ethylene butylene-styrene block copolymer). If desired, the earlier form of the apparatus of the invention as shown in FIGS. 1 through 9 can alternatively have a fill means such as shown in FIG. 17 to permit filling in the field. As best seen by referring to FIG. 12, passageway 70 is in communication with a pair of longitudinally extending passageways 74 formed in element 60. Passageways 74 are in turn in communication with chamber 25 via passageways 76.

Cover 80 is formed of a clear plastic material which is impermeable to fluid including gases. This type of cover is used when the medicinal agent within chamber 25 is such that it must be sealed with respect to atmosphere. As best seen in FIG. 10 cover 80 is provided with a pair of longitudinally extending protuberances 82 which are interconnected by a web 84. Web 84 carries on its upper surface an impermeable barrier peel strip 86 that covers vent means provided in web 84 to enable venting of chamber 25 at time of use.

The apparatus of this second form of the invention includes a needle assembly 42 of similar function and construction as that previously described and includes a shielded injection needle 46. The needle assembly is provided with web means and a frangible section 42c to enable portion 42b of the needle assembly to be removed in the manner shown in FIG. 16.

Figure 12:
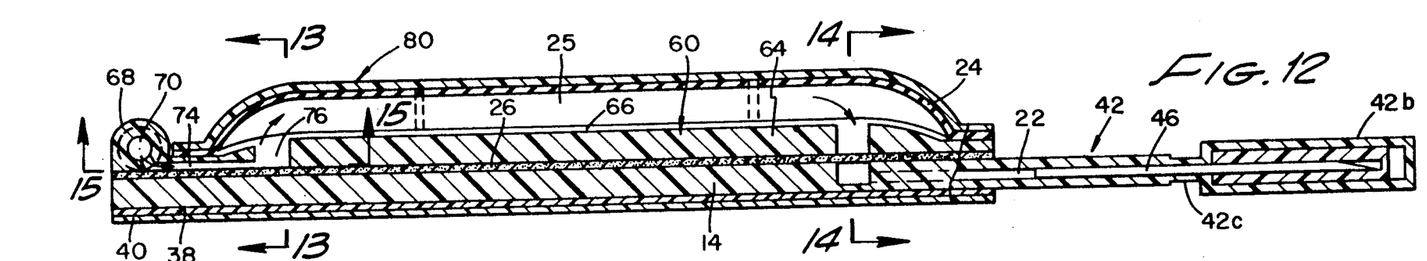
FIG. 12 is a cross sectional view taken along lines 12—12 of FIG. 11.
Figures 13, 14, 15, 16:
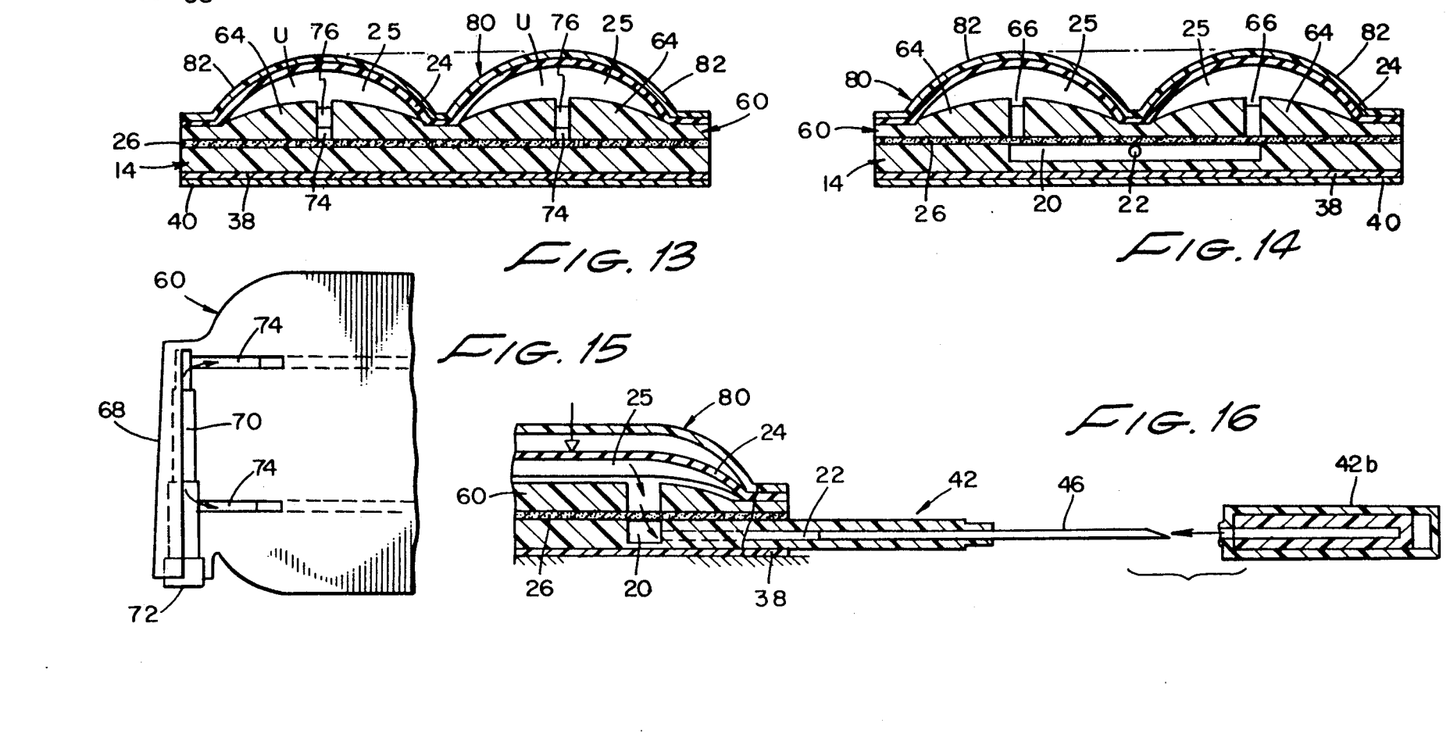
FIG. 13 is a cross sectional view taken along lines 13—13 of FIG. 12.
FIG. 14 is a cross sectional view taken along lines 14—14 of FIG. 12.
FIG. 15 is a fragmentary view taken along lines 15—15 of FIG. 12.
FIG. 16 is a view similar to FIG. 12, but showing the molded needle cover separated from the device.

As before, so long as needle assembly 42 remains intact in the manner shown in FIG. 12, the fluid will be retained within chamber 25. However, upon twisting off the frangible section 42c so that portion 42b on the needle assembly can be removed as shown in FIG. 16, distendable membrane 24 will begin to expel fluid through the needle 46. The rate of expulsion of fluid is, of course, controlled by the permeable membrane 26 which is disposed intermediate the fluid flow passageways 66 of member 60 and fluid flow passageways 16 and 18 formed in base 14.

Referring to FIGS. 18 through 21, another embodiment of the invention is thereshown. The apparatus of this form of the invention is similar in many respects to the embodiment shown in FIGS. 1 through 9 and like numbers are used to identify like components. Unlike the apparatus illustrated in FIGS. 1 through 9, the apparatus of this third form of the invention does not embody an injection needle assembly. Rather, the device of this embodiment includes a luer connector assembly 90, the function of which will presently be described.

Figures 18, 19:
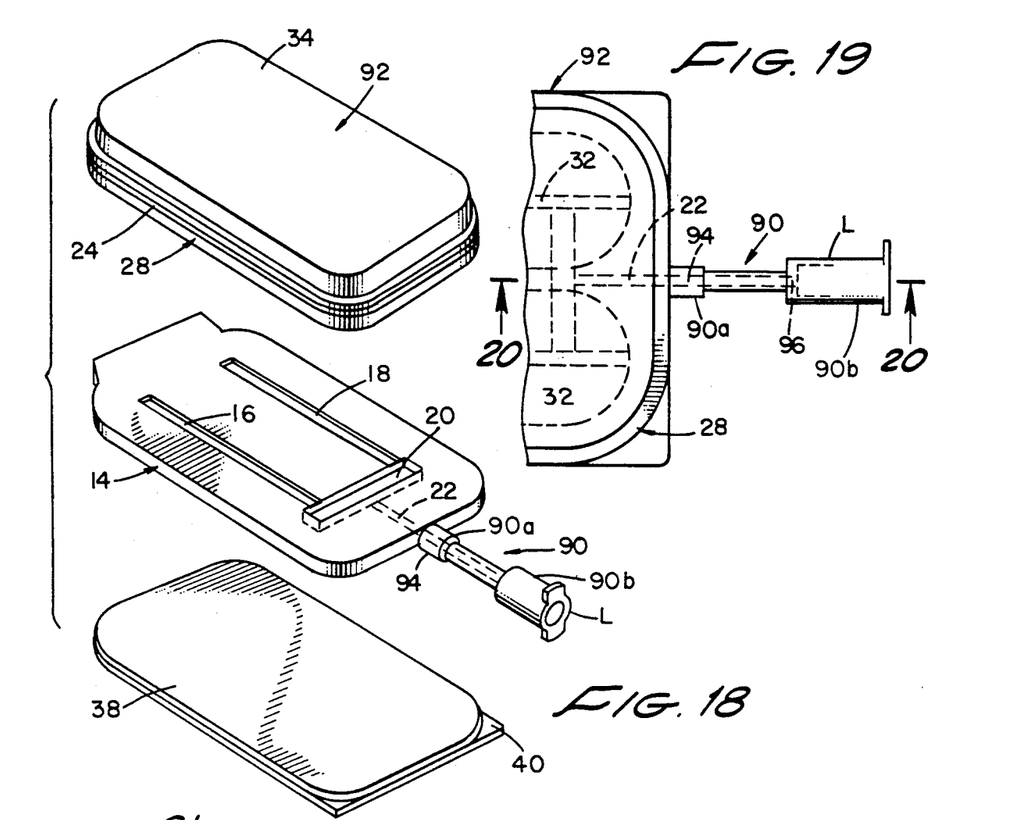
FIG. 18 is a generally perspective exploded view of another embodiment of the apparatus of the present invention.
FIG. 19 is a fragmentary top view of the apparatus of this form of the invention.

Turning particularly to FIG. 18, the apparatus can be seen to comprise a base 14, and an operating assembly 92 associated therewith comprising a distendable member 24, a distendable member engaging element 28, a flow control member 26 and a cover 34, all of which are of the same general character and function in the same manner as the embodiment of the invention shown in FIGS. 1 through 9. The device also includes an adhesive foam pad 38 and a peel strip 40 carried by base 14.

Figure 20:
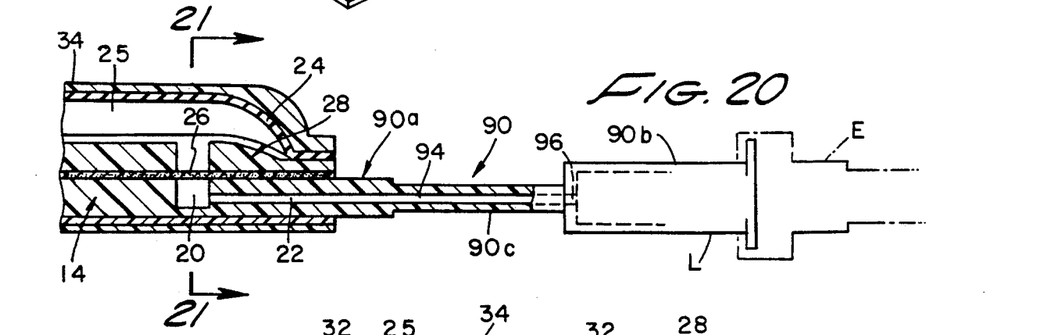
FIG. 20 is a cross sectional view taken along lines 20—20 of FIG. 19.

The luer connector assembly 90, which comprises the distinguishing feature of this form of the invention, is integrally formed with base 14 and includes a distal portion 90a and a proximal portion 90b. Distal portion 90a is provided with a longitudinally extending bore 94 which communicates with outlet 22 of base 14. Comprising the proximal portion 90b of assembly 90 is a luer connector of standard construction having a fluid passageway 96 which communicates with bore 94 of distal portion 90a. The outlet of passageway 96 is sealed by a frangible closure which is removable to activate fluid flow. The outboard end of distal portion 90a, designated in the drawings as 90c is of reduced diameter and is readily flexed to permit easy connection of the luer connector "L" with an external system "E" (FIG. 20).

Figure 21:
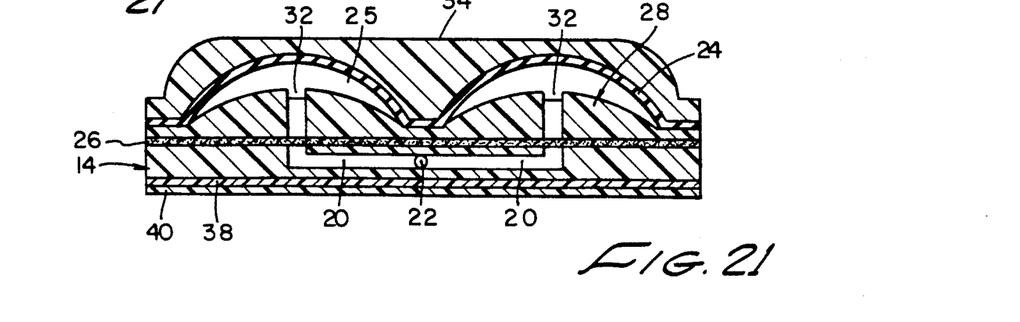
FIG. 21 is a cross sectional view taken along lines 21—21 of FIG. 20.

As shown in FIGS. 18 and 21, base 14 includes fluid conduits 16, 18 and 20 which communicate with outlet passageway 22. Distendable membrane 24 functions to expel fluid from chamber 25, through flow rate control member 26 and outwardly through outlet passageway 22 in the manner previously described.

Referring to FIGS. 22 through 29 yet another form of the invention is shown and identified by the numeral 100. For certain medicinal agents, it is desirable to provide an initial high rate delivery followed by a slower rate sustained delivery. This form of the invention permits this to be accomplished. The apparatus of this form of the invention is similar in many respects to the embodiment shown in FIGS. 1 through 9 and like numbers are used to identify like components. Unlike the apparatus illustrated in FIGS. 1 through 9, the apparatus of this fourth form of the invention is not limited to a fixed rate infusion of the medicinal agent. Rather, because of the novel configuration of the distendable membrane engaging element and the dual flow rate control members of this form of the invention, a controlled variable rate of fluid flow is possible.

Figures 22, 24:
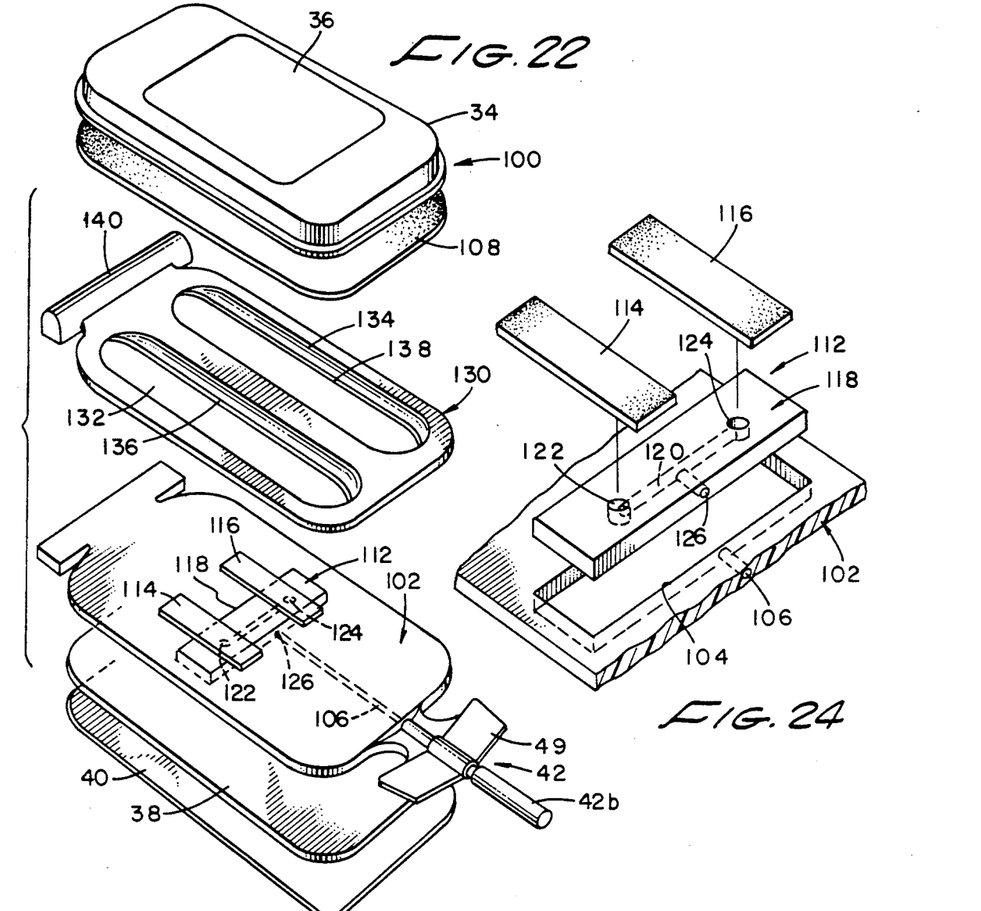
FIG. 22 is a generally perspective exploded view of still another form of the apparatus of the present invention.
FIG. 24 is a greatly enlarged fragmentary perspective view of a portion of the apparatus illustrating the arrangement of the rate control membranes of the device.
Figure 23:
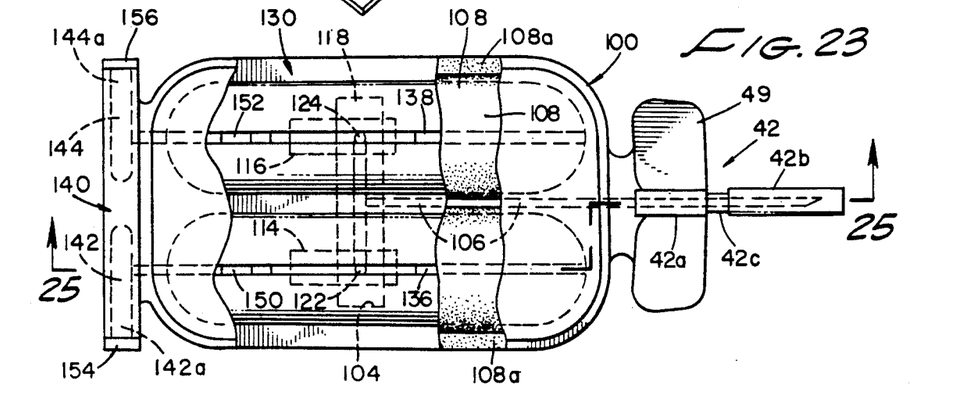
FIG. 23 is a plan view of the apparatus of FIG. 22 partly broken away to show internal construction.
Figure 25:
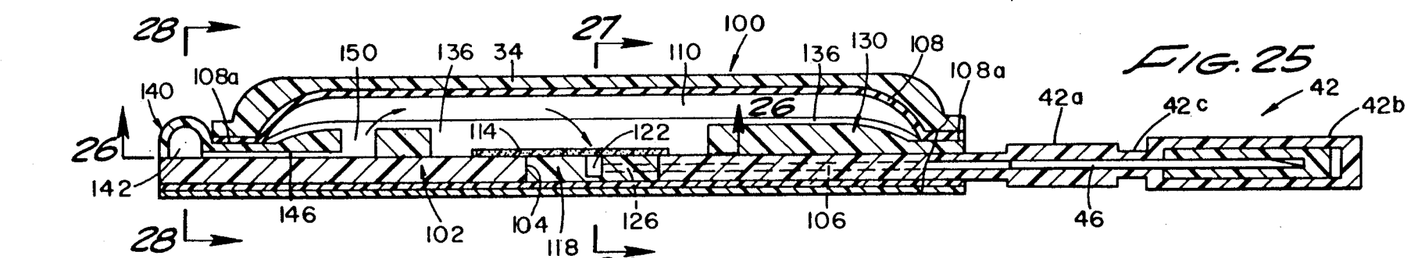
FIG. 25 is a cross sectional view taken along lines 25—25 of FIG. 23.
Figures 26, 27, 28, 29:
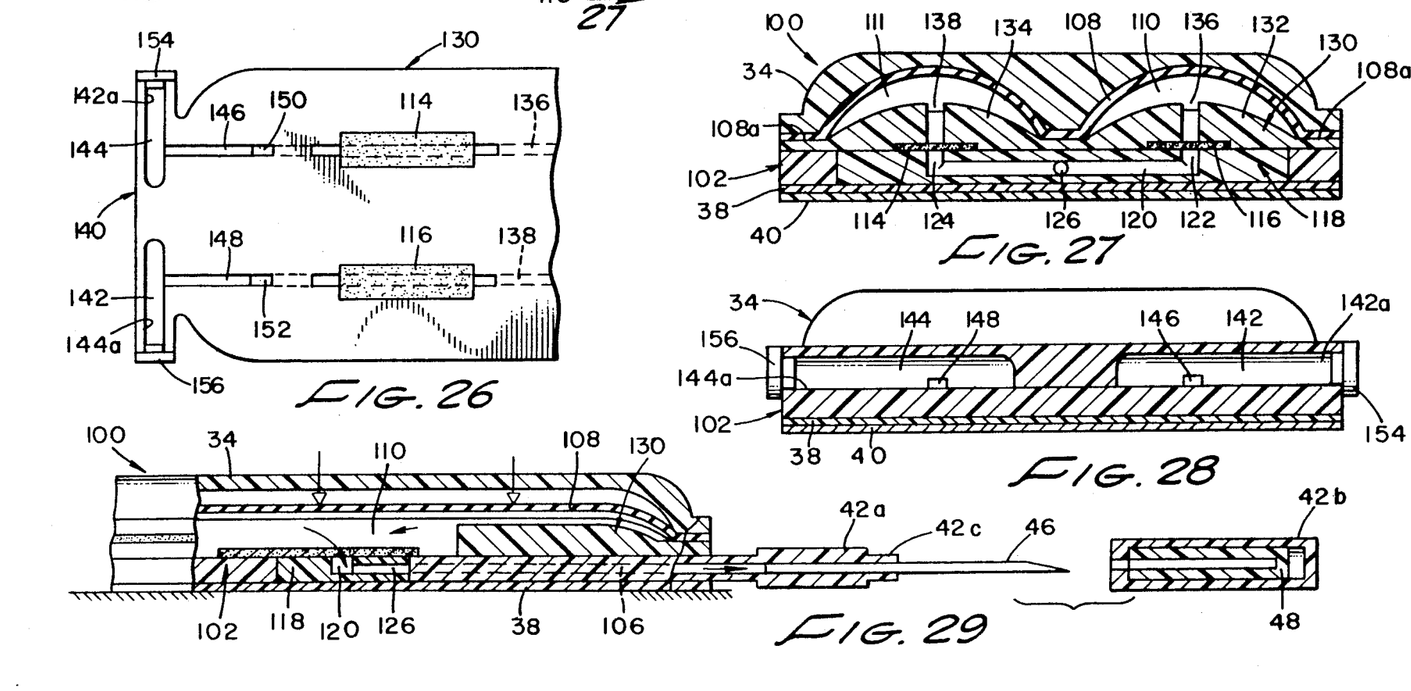
FIG. 26 is a fragmentary view taken along lines 26—26 of FIG. 25.
FIG. 27 is a cross sectional view taken along lines 27—27 of FIG. 25.
FIG. 28 is a cross sectional view taken along lines 28—28 of FIG. 25.
FIG. 29 is a fragmentary, cross sectional view similar to FIG. 25, but showing the needle cover separated from the apparatus of the invention.

As best seen in FIGS. 22, 23 and 24, the apparatus of this last form of the invention also comprises a laminate, or layered, structure made up of a plurality of thin plate-like components. The apparatus includes a thin, generally planar plate-like base 102, having a transverse recess 104 in communication with a fluid outlet passageway 106. A thin, generally planar elastic distendable membrane, or member 108 cooperates with base 102 to form a pair of discrete chambers 110 and 111 (FIG. 27). For certain applications, Chambers 110 and 111 may be of different individual size and configuration each having different volumes. As before, member 108 is distendable out of plane in the manner shown in FIG. 25 by the introduction of fluid into the chambers under pressure. The method of introduction of fluids into chambers 110 and 111 will presently be described.

Forming an important aspect of the apparatus of this fourth form of the invention is the provision of flow control means which are disposed internally of chambers 100 and 111 for controlling the rate of fluid flow of fluid from each chamber through outlet 106. In the embodiment of the invention hereshown, the flow control means is provided in the form of a flow rate control assembly 112 which is received within recess 104 formed in base 102 in the manner shown in FIGS. 22 and 24. Flow rate control assembly 112 includes a pair of permeable members 114 and 116 which, as will presently be described, precisely control the rate of fluid flow from chambers 110 and 111 into fluid outlet 106. Passageway 106 is in communication with the fluid passageway of needle assembly 42 which is of the same construction as previously described herein.

As best seen in FIG. 24, assembly 112 comprises a manifold member 118 which is closely receivable within recess 104 formed in base 102. Member 118 is provided with an internal fluid conduit 120 having fluid inlets 122 and 124 at either end and a fluid outlet 126 proximate its center. Outlet 126 is adapted to communicate with outlet passageway 106 provided in base 102 when member 118 is in position within recess 104. Permeable members 114 and 116 overlay inlets 122 and 124 and, in a manner presently described, control the flow of fluid into these outlets from chambers 110 and 111. Fluid inlets 122 and 124, can be constructed in various geometries and, in cooperation with the ullage means, presently to be described, to provide various degrees of active surface area of the rate control membrane.

The distendable member engaging element 130 of this latter form of the invention is of slightly different construction and includes filling means which enable chambers 110 and 111 to be filled separately. As best seen in FIGS. 22 and 25, element 130 is superimposed over base 102 and flow control assembly 112 and includes a pair of longitudinally extending, spaced apart upstanding protuberances 132 and 134. Protuberances 132 and 134 are provided with fluid passageways 136 and 138 respectively. Passageway 136 communicates with fluid inlet 122 and passageway 138 communicates with inlet 124 of assembly 112. By varying the configuration of these passageways and fluid inlets alternate active surface areas of the flow control membrane can be exposed. Element 130 also includes an upstanding transversely extending portion 140 having a pair of fluid passageways 142 and 144 extending from the open ends 142a and 144a thereof. As shown in FIG. 23, passageway 142 is in communication with passageway 136 of element 130 via a passageway 150 and passageway 144 is in communication with passageway 138 of element 130 via a passageway 148. Passageways 152 and 148, in turn, communicate with chambers 110 and 111, respectively, via passageways 150 and 152 respectively (see FIGS. 25 and 26). Open ends 142a and 144a of passageways 142 and 144 are closed by any suitable means such as heat sealing.

The apparatus of this fourth embodiment of the invention is adapted to be filled with the selected medicinal fluid at time of manufacture. This is accomplished by forcing fluid under pressure into passageways 142 and 144, and thence, into chambers 110 and 111 via passageways 150 and 152. As the fluid under pressure flows into the two chambers, it will cause the membrane 108 to distend upwardly into engagement with cover 34 in the manner shown in FIG. 27. After chambers 110 and 111 have been filled with the selected medicinal fluid, passageways 142 and 144 are sealably closed. Cosmetic closure plugs 154 and 156 can be used if desired at the ends of conduits 142 and 144. It is to be observed that membrane 108 is bonded along its margins 108a to member 130 and is in sealable engagement along its longitudinal center line with member 130 intermediate protuberances 132 and 134. With this construction, chambers 110 and 111 are maintained independent from one another.

Upon twisting off the frangible section 42c so that portion 42b on the needle assembly can be removed as shown in FIG. 29, elastic distendable membrane 108 will begin to expel fluid through flow control members 114 and 116. The rate of flow of fluid is, of course, controlled by the degree of permeability of each of the members 114 and 116. If one of these members has a greater permeability than the other, fluid will flow through that member at a greater rate. Accordingly, by varying the permeability of members 114 and 116, and with the output summed via flow channels 120 and 106, a larger initial volume of fluid can be injected into the patient. Continuous injection of fluid at a slower controlled rate will then follow. For example, if member 114 has a high degree of permeability, fluid will be forced out of chamber 110 at a rapid rate. On the other hand, if member 116 has a low permeability, fluid will be forced out of chamber 111 at a slower rate. With this arrangement, fluid can be simultaneously injected initially at a high rate from chambers 110 and 111 then at a much slower rate from chamber 111.

As indicated in FIG. 22, the apparatus is closed by a cover 34 having a medicant label 36. If a barrier cover and base configuration is used, cover vent means as previously described, must be provided. Affixed to the bottom of the base is an adhesive foam pad 38 and a peel strip 40 so that the apparatus can be self-attached to the patient.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A device for expelling fluids at a controlled rate comprising:
   (a) a base having a width;
   (b) a distendable membrane constructed of an elastic material which is fitted over said base to form a chamber having a fluid outlet and a height substantially less than said width of said base, said distendable membrane being distendable in a manner to establish internal stresses therewithin tending to return said membrane to a less distended configuration, whereby fluid will be urged to flow from said fluid outlet; and
   (c) flow control means disposed internally of said chamber for controlling the rate of flow of fluid through said outlet, said flow control means comprising a thin permeable member superimposed over said base.

2. A device as defined in claim 1 further including distendable membrane engagement means, disposed intermediate said distendable membrane and said flow control means, for engagement with said distendable membrane 3. A device as defined in claim 2 further including a cover superimposed over said base, said distendable membrane, said distendable membrane engagement means and said flow control means.

4. A device as defined in claim 2 in which said base is generally plate-like in configuration, having at least one fluid flow channel formed therein for conducting fluid toward said outlet.

5. A device as defined in claim 4 in which said distendable membrane engagement means comprises a body portion and at least one upstanding protuberance having a fluid flow opening therein in communication with said fluid flow channel.

6. A device as defined in claim 5 in which said base, said distendable membrane, said distendable member engagement means and said flow control means are yieldably deformable.

7. A device as defined in claim 5 further including a hollow needle operably interconnected with said outlet of said chamber.

8. A device as defined in claim 5 further including a fluid outlet passageway interconnected with said outlet of said chamber and connection means interconnected with said fluid outlet passageway for permitting said device to be connected to an external system.

9. A device for use in infusing pharmaceutical fluids into an ambulatory patient at a controlled rate comprising;
   (a) a plate-like base having at least one fluid conduit formed therein, said fluid conduit terminating in a fluid outlet;
   (b) a distendable membrane constructed of an elastic material which is fitted over said base to define a chamber, said membrane being at least partially under tension, being distendable by liquid introduced into said chamber under pressure and having a tendency to return to a substantially non-deformed configuration;
   (c) at least one fluid flow control means disposed internally of said chamber for controlling the rate of flow of fluid toward said fluid conduit;
   (d) means disposed intermediate said distendable membrane and said fluid flow control means for creating an ullage within said chamber; and
   (e) infusion means connected to said fluid outlet for infusing fluid into the patient.

10. A device as defined in claim 9 further including filling means connected to said base for introducing fluid under pressure into said fluid chamber.

11. A device as defined in claim 9 in which said fluid flow control means comprises a thin film, planar shaped permeable membrane.

12. A device as defined in claim 10 in which said base is provided with first and second fluid conduits and in which said fluid flow control means comprises first and second permeable members operably associated with said first and second fluid conduits respectively, each of said permeable members having different permeability, whereby the rate of fluid flow through each of said fluid conduits is controllably regulated.

13. A device as defined in claim 10 in which said base and said permeable membrane are yieldably deformable.

14. A device as defined in claim 10 in which said infusion means comprises a hollow needle.

15. A device as defined in claim 14 in which said hollow needle is integral with said base.

16. A device as defined in claim 15 further including an integrally formed web member and needle cover connected to said base, said needle cover being separable from said web member.

17. A device as defined in claim 16 further including adhesive means connected to said base for releasably interconnecting said base to the anatomy of the patient.

18. A device for use in infusing medicinal fluids into a patient at a controlled rate comprising:
   (a) a thin, generally planar base having a fluid conduit formed therein, said fluid conduit terminating in a fluid outlet;
   (b) means for forming a fluid chamber comprising a thin, generally planar distendable film member superimposed over said base, said member being distendable out of plane by liquid introduced into said fluid chamber under pressure to establish internal stresses in said member said stresses tending to return said member to a less distended configuration;
   (c) a thin, generally planar, permeable member of a size substantially corresponding to the size of said base disposed internally of said chamber for controlling the flow of fluid toward said fluid conduit in said base;
   (d) a distendable film member engaging element disposed within said chamber intermediate said permeable member and said distendable film member, said distendable film member engaging element comprising an upstanding protuberance provided with a fluid flow chamber in communication with said fluid conduit in said base; and
   (e) a hollow needle integrally formed with said base in operable communication with said fluid outlet.

19. A device as defined in claim 18 in which said distendable film member is permeable to gases.

20. A device as defined in claim 18 in which said distendable film member is at least partially bonded to said distendable film member engaging element.

21. A device as defined in claim 18 in which said distendable film member engagement element is provided with filling means for introducing fluid into said chamber.

22. A device as defined in claim 21 in which said filling means comprises:
   (a) a fluid passageway formed in said distendable film member engaging element having first and second ends, said first end being in communication with said fluid conduit in said base; and
   (b) septum means mounted within said second end of said fluid passageway for receiving therethrough a needle of a hypodermic syringe.

23. A device as defined in claim 22 further including adhesive means connected to said base for removably connecting said device to the patient's anatomy.

24. A device as defined in claim 23 in which said base, said distendable film member and said distendable film member engaging element are flexible yieldably deformable out of plane.

25. A device as defined in claim 24 further including a sheet of foam disposed intermediate said adhesive means said base.

26. A device for expelling fluids at a controlled rate, comprising:
   (a) a base;
   (b) means for forming a fluid chamber comprising a distendable membrane constructed of an elastic material superimposed over said base;
   (c) flow control means disposed internally of said chamber for controlling the rate of flow of fluid through said outlet, said flow control means comprising a thin permeable member superimposed over said base;
   (d) distendable membrane engagement means, disposed intermediate said distendable membrane and said flow control means, for engagement with said distendable membrane; and (e) a cover superimposed over said base, said distendable membrane, said distendable membrane engagement means and said flow control means.

27. A device for expelling fluids at a controlled rate, comprising:

(a) a base having a width and first and second surfaces;

(b) means for forming a fluid chamber comprising a distendable membrane constructed of an elastic material spanning said first surface of said base, said fluid chamber having a fluid outlet and being of a height substantially less than said width of said base, said distendable membrane being distendable in a manner to establish internal stresses therewithin tending to return said membrane to a less distended configuration whereby fluid will be urged to flow from said fluid outlet; and (c) flow control means disposed internally of said chamber for controlling the rate of flow of fluid through said fluid outlet.

28. A device as defined in claim 27 in which said distendable membrane includes edge portions and in which said first and second surfaces of said base are substantially planar, said first surface being disposed within said chamber and said second surface being disposed exteriorly of said chamber.

29. A device as defined in claim 28 in which said fluid chamber is bounded by said first surface of said base and said edge portions of said distendable membrane, said fluid chamber being substantially arch-shaped in cross-section.

30. A device as defined in claim 27 further including means disposed intermediate said distendable membrane and said flow control means for creating ullage within said chamber.

31. A device for expelling fluids at a controlled rate, comprising:

(a) a plate-like base having first and second surfaces;

(b) means for forming a fluid chamber having a fluid outlet comprising a sheet-like distendable membrane constructed of an elastic material spanning said first surface of said base, said distendable membrane being terminally bound to said first surface of said base and being distendable in a manner to establish internal stresses therewithin tending to return said membrane to a less distended configuration whereby fluid will be urged to flow from said fluid outlet; and (c) flow control means disposed internally of said chamber for controlling the rate of flow of fluid through said outlet.

32. A device as defined in claim 31 in which a substantial portion of said first surface of said base is disposed internally of said fluid chamber and in which said second surface of said base is disposed externally of said fluid chamber.

* * * * *